United States Patent [19]

Koji

[11] Patent Number: 4,899,057
[45] Date of Patent: Feb. 6, 1990

[54] SANITARY DEVICE

[75] Inventor: Masashi Koji, Shinjuku, Japan

[73] Assignee: Hoshin Kagaku Sangyosho Co., Ltd., Tokyo, Japan

[21] Appl. No.: 364,561

[22] Filed: Jun. 7, 1989

Related U.S. Application Data

[63] Continuation of Ser. No. 144,033, filed as PCT JP87/00187 on Mar. 26, 1987, published as WO87/05811 on Oct. 8, 1987, abandoned.

[30] Foreign Application Priority Data

| Mar. 26, 1986 | [JP] | Japan | 61-67451 |
| Mar. 26, 1986 | [JP] | Japan | 61-67452 |
| Mar. 26, 1986 | [JP] | Japan | 61-67453 |
| Mar. 26, 1986 | [JP] | Japan | 61-67454 |

[51] Int. Cl.$^4$ ............................. A61L 2/10
[52] U.S. Cl. ............... 250/436; 250/455.1; 250/432 R; 250/435; 422/24; 210/748
[58] Field of Search ............. 250/455.1, 432 R, 435, 250/436; 422/24; 210/748

[56] References Cited

U.S. PATENT DOCUMENTS

| 2,146,688 | 2/1939 | Selig | 250/455.1 |
| 2,822,476 | 2/1958 | Osgood | 250/455.1 |
| 3,100,842 | 8/1963 | Tellefsen | 250/455.1 |
| 4,063,890 | 12/1977 | Baron | 422/24 |
| 4,088,445 | 5/1978 | Ellis | 250/455.1 |
| 4,103,167 | 7/1978 | Ellner | 250/423 R |
| 4,121,107 | 10/1978 | Bachmann | 250/455.1 |
| 4,661,264 | 4/1987 | Goudy | 210/748 |
| 4,774,415 | 9/1988 | Biegel et al. | 250/455.1 |

FOREIGN PATENT DOCUMENTS 50-685 1/1975 Japan.

OTHER PUBLICATIONS

*Websters Ninth New Collegiate Dictionary*, 1986, p. 356.

Primary Examiner—Jack I. Berman
Attorney, Agent, or Firm—Bauer & Schaffer

[57] ABSTRACT

A sanitary device, wherein elements (6) for emitting rays of light which can prevent proliferation of bacteria are disposed in relation to objects (1, 14, 17 and 31) which are to be maintained in a sanitary condition can make it possible, by irradiating the objects by means of the elements to prevent bacteria from proliferating, to maintain efficiently objects, which should be kept in a sanitary state, in the sanitary condition. When compared with the use of an ultraviolet lamp, this device requires less space and has better efficiency and a lifetime of more than ten times that of the lamp.

18 Claims, 4 Drawing Sheets

SANITARY DEVICE

This is a continuation of Ser. No. 144,033 filed as PCT JP87/00187 on Mar. 26, 1987, published as WO87/05811 on Oct. 8, 1987, now abandoned.

TECHNICAL FIELD

The present invention relates generally to a sanitary device suitable for use with a tank of relatively small capacity (or small size) for keeping therein liquid to be maintained in a clean, sanitary condition or for letting such liquid flow out therefrom, a container for accommodating therein goods such as tooth brushes, combs and so on that should be maintained in a clean condition, a nozzle for letting sterilized water, drinking water or the like to be maintained in a sanitary, clean condition flow out therethrough, a pipe for supplying therethrough various kinds of drinks which are to be protected from being contaminated by bacteria or the like.

BACKGROUND ART

So far ultraviolet lamps have been used to sterilize or disinfect various kinds of things. The ultraviolet lamp for use with a small capacity tank has a lifetime as long as 2000 to 3000 hours under the continuous driving condition or it has a lifetime one half of the above-mentioned lifetime under the intermittent driving condition. Further, due to the sizes of a glow tube and a stabilizer for actuating itself, the ultraviolet lamp becomes large in size in view of a small capacity tank. Thus, it is difficult to make the ultraviolet lamp compact in size. Also, in an automatic vending machine for vending drinks, for example, such means is not yet used that keeps a supplying pipe for supplying various kinds of drinks clean.

All of tanks of small capacity used as a water purifier and an automatic drink vending machine, water tanks used as a purified water container, a humidifier, a dehumidifier and an air cleaner, a water container for holding a contact lens and various kinds of small water supplying tanks must be kept clean and in good sanitary condition. If the ultraviolet lamp is utilized to sterilize the inside of such small tank, since it is difficult to minimize the lamp due to the above-mentioned reason, the ultraviolet lamp radiates even the unnecessary portion of the tank, which fact is uneconomical. Also, it is very difficult to mount such ultraviolet lamp on the tank.

Preferably, the inside of containers for tooth brushes, combs and so on should be maintained in a clean, sanitary condition and also, articles to be kept in the container must be kept clean. If the ultraviolet lamp is used to sterilize such container of relatively small size, the lamp cannot be made compact in size due to the above mentioned reasons so that the lamp irradiates the unnecessary portion of the tank which fact is uneconomical and that the lamp cannot be mounted to the container itself.

Also, it is desirable that a pipe-shaped portion (hereinafter generally referred to as a nozzle) through which sterilized water and drinking water are supplied be maintained in a sanitary, clean condition. If the ultraviolet lamp is used to sterilize such small, restricted portion, the ultraviolet lamp cannot be made compact in size due to the above-mentioned reason so that it irradiates the unnecessary portion, which fact is uneconomical and that it cannot be mounted to the nozzle without difficulty.

Further, if the ultraviolet lamp is used to sterilize the drink supplying pipe of the automatic drink vending machine or the like, the ultraviolet lamp cannot be made compact in size due to the above-mentioned reasons so that it occupies a large space, and also there may be a fear that the lamp is broken and that a harmful insect enters the vending machine.

DISCLOSURE OF INVENTION

Accordingly, a first object of the present invention is to efficiently prevent various kinds of small tanks from being contaminated by bacteria by a simple method.

That is, in view of such a fact that visible light, infrared rays or ultraviolet rays included in rays of light emitted from a light emission diode act,, to prevent bacteria from proliferating, the light emission diode is disposed so as to irradiate the inside of the small tank to thereby prevent the inside of the tank from being contaminated. Thus, the proliferation of bacteria is suppressed at the portion irradiated by rays of light emitted from the light emission diode so that the inside of the small tank can be kept under a sanitary, clean condition.

A second object of this invention is to efficiently keep the inside of a container of relatively small size maintained in a sanitary, clean condition by a simple method.

That is, in view of such a fact that visible light, infrared rays or ultraviolet rays included in rays of light emitted from a light emission diode act to prevent bacteria from proliferating, the light emission diode is so disposed on the container itself as to irradiate the inside of the container thereby to prevent articles kept in the container from being contaminated by bacteria. Thus, bacteria is suppressed from proliferating at the portion irradiated by rays of light emitted from the light emission diode so that the inside of the container and the articles within the container can be maintained in a sanitary, clean condition.

A third object of the present invention is to efficiently prevent mouths of various nozzles from being contaminated by bacteria by a simple method.

That is, in view of such a fact that visible light, infrared rays or ultraviolet rays included in rays of light emitted from a light emission diode act to prevent bacteria from proliferating, the light emission diode is so disposed as to irradiate at least the mouth of the nozzle to thereby prevent that portion from being contaminated by bacteria. Thus, bacteria are suppressed from proliferating at the portion irradiated by rays of light emitted from the light emission diode so that the mouth of the nozzle can be kept in a sanitary, clean condition.

A fourth object of the present invention is to maintain a drink supplying pipe used in the automatic drink vending machine or the like in a sanitary condition by a small-sized light source of long lifetime.

That is, in view of such a fact that visible light, infrared rays or ultraviolet rays included in rays of light emitted from a light emission diode act to prevent the proliferation of bacteria, a pipe for supplying various kinds of drinks is made of light transmission material and a light emission diode is disposed around the pipe thereby to prevent the drink supplying pipe from the contamination. Thus, the drink supplying pipe having light transmission property is irradiated to its inside by the light emission diode and bacteria are suppressed from proliferating thereat so that the drink supplying pipe can be kept in a sanitary condition.

BEST MODE FOR CARRYING OUT THE INVENTION

Figure 1:
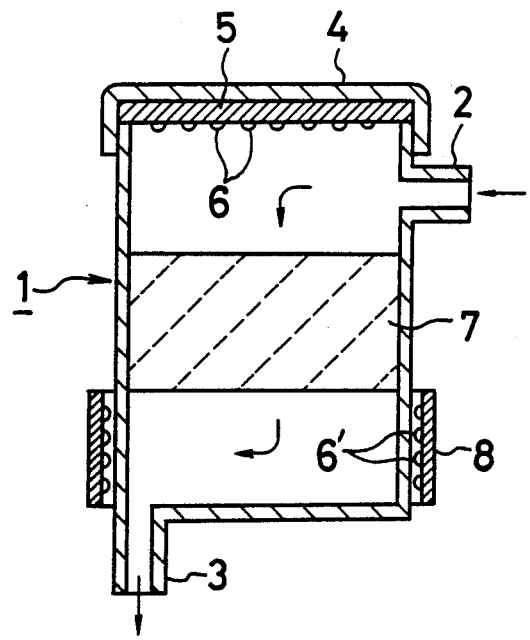
FIG. 1 is a cross-sectional view illustrating the first embodiment of the present invention.

FIG. 1 is a cross-sectional view illustrating the first embodiment in which the present invention is applied to a water purifier. Referring to the figure, a water purifier 1 generally comprises a water entrance 2, a water exit 3, a lid 4, an inner base plate 5, light emission diodes 6 and 6', a filter 7 and an outer base plate 8. Such water purifier 1 can be regarded as a kind of small tank. The outer form of the tank may be either columnar or cubic. The form of the lid 4 may be circular if the outer form of the tank is columnar and may be rectangular if it is cubic. To the rear side of the lid 4, there is fixed the base plate 5 having the light emission diodes 6 mounted thereon. The light emission diodes 6 are arranged to irradiate the water purifier at its portion nearer to the entrance side (primary side) than the filter 7. The outer base plate 8 may be annular if the outer form of the tank is columnar and may be rectangular-annular if it is of a rectangular-ring. The light emission diodes 6' mounted to the inside of the outer base plate 8 irradiate the portion of the tank nearer to the exit side (secondary side) than the filter 7. In this embodiment, the tank must be made of material having light transmission property at least at its portion around which the light emission diodes 6' are located. If there are provided only the light emission diodes 6', it is not necessary to make the tank by the material having light transmission property. The light emission diodes 6, 6' are coated with a proper protective film having light transmission property.

Figure 2:
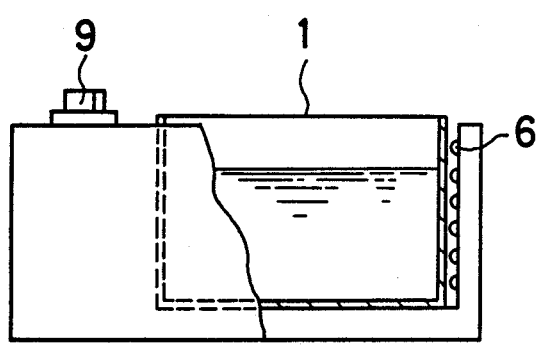
FIG. 2 is a cross-sectional view of a main portion illustrating the second embodiment of the present invention.

FIG. 2 is a cross-sectional view showing a main portion of the second embodiment in which the present invention is applied to a humidifier. Referring to the figure, this humidifier comprises a water tank 1 for the humidifier, light emission diodes 6 and a volume control 9. Also in this embodiment, the tank 1 must be made of material having light transmission property at its portion opposing to the light emission diodes 6. In this way, the light emission diodes irradiate the inside of the tank from the side surface.

Figure 3:
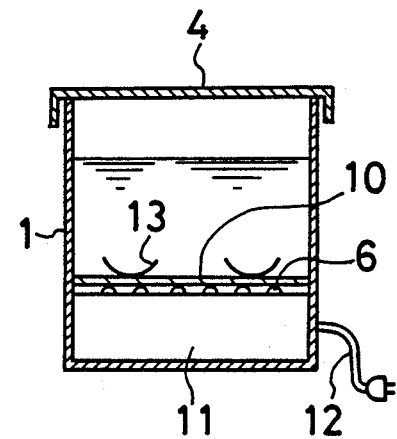
FIG. 3 is a cross-sectional view illustrating the third embodiment of the present invention.

FIG. 3 is a cross-sectional view illustrating the third embodiment of the present invention which is applied to a water receptacle for a contact lens. Referring to the figure, this water receptacle for a contact lens comprises a water receptacle 1, a lid 4, light emission diodes 6, a partition plate 10, a power supply source apparatus 11, a power cord 12 and a contact lens 13. In this embodiment, the inside of the water receptacle 1 is irradiated from its underside so that the partition plate 10 must be made of material having light transmission property. While the power supply source apparatus 11 includes a transformer and a rectifier, the power supply source may be a battery (or a rechargeable battery).

In the first to third embodiments as described above, it may be possible to confirm by providing light receiving elements opposed to the light emission diodes and an indication lamp outside the tank whether or not the light emission diodes are being driven to actually emit rays of light.

Figure 4:
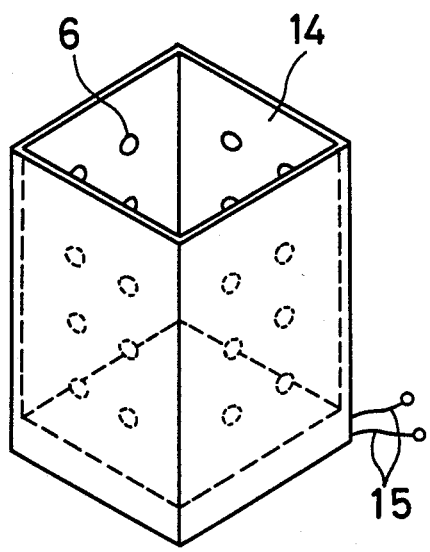
FIG. 4 is a perspective view illustrating the fourth embodiment of the present invention.

FIG. 4 is a perspective view illustrating the fourth embodiment in which the present invention is applied to a rectangular-shaped container. Referring to the figure, there is provided a container 14. The light emission diodes 6 are arranged on a base plate (not shown) installed on the inner surface of the container 14 and are connected in parallel to a power supply source. The light emission diodes 6 are coated with a proper protective film. Such container 14 may contain therein, in addition to the tooth brushes and the combs, a glass, a cap of microphone and so on which are touched by the user with mouth. If the articles to be contained in this container are made of material having light transmission property, better effects can be achieved. While in the illustrated example the light emission diodes 6 are arranged on the inner surface of the container 14, they may be provided on the bottom surface thereof. While the number of light emission diodes 6 is varied dependent on the output of each diode, the number thereof can be decreased because the output from the light emission diode can be increased by the pulse oscillation having a large amplitude.

Figure 5:
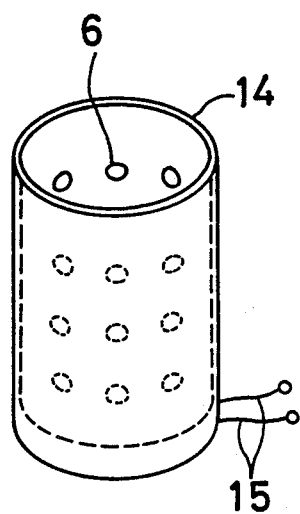
FIG. 5 is a perspective view illustrating the fifth embodiment of the present invention.

FIG. 5 is a perspective view illustrating the fifth embodiment of the present invention which is applied to a cylindrically-shaped container. In the figure, like parts corresponding to those of FIG. 4 are marked with the same references. In the case of the cylindrically-shaped container, the light emission diodes 6 must be located with great care. For example, only the portions thereof to which the light emission diodes 6 are mounted are each made flat or the container 14 is formed as a polygonal column. Other portions are arranged similar to those of FIG. 4.

Figure 6:
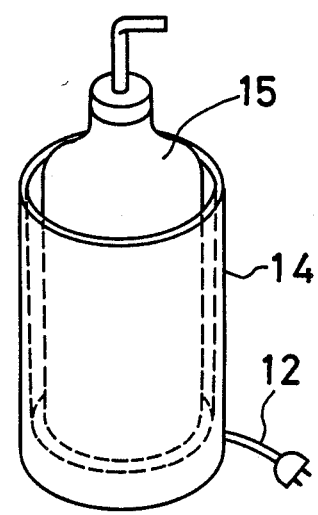
FIG. 6 is a perspective view illustrating an example of how to use the embodiment shown in FIG. 5.

FIG. 6 is a perspective view illustrating an example in which the container of the type shown in FIG. 5 is used actually. The light emission diodes 6 are not shown in FIG. 6. There is provided a bottle of light transmission property which contains purified water. The power supply source may be a commercially-available power supply source or a battery.

While both in the fourth and fifth embodiments the light emission diodes 6 are provided on the inner surface of the container 14, the container 14 may be made of material having light transmission property and the light emission diodes may be arranged around the outer periphery of the container.

Figures 7A, 7B, 7C:
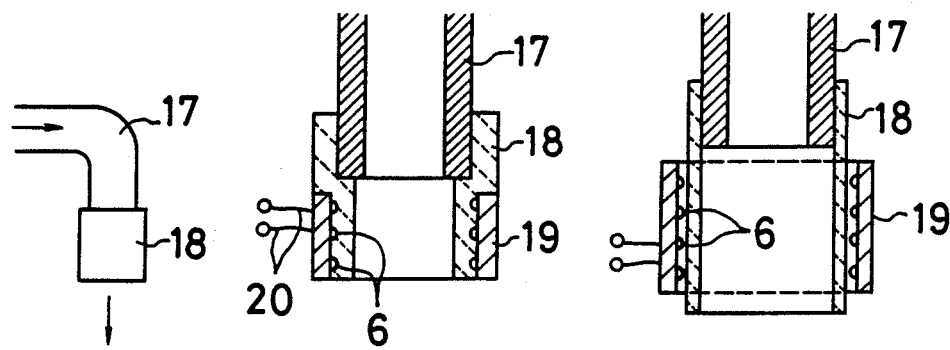
FIG. 7 is a diagram and cross-sectional view illustrating the sixth embodiment of the present invention.

FIG. 7 illustrates the sixth embodiment of the present invention, in which FIG. 7A is a diagram showing the appearance thereof, FIG. 7B is a cross-sectional view illustrating the main portion thereof and FIG. 7C is a cross-sectional view illustrating a modified example thereof. Throughout these figures, reference numeral 17 designates a nozzle from which drinking water or germless water is flowed out, 18 a cylindrically-shaped ring engaged with the top of the nozzle, 19 an insulating base plate and 20 lead wires. The cylindrically-shaped ring 18 is made of, for example, material having light transmission property and is formed together with the base plate 19 and the light emission diodes 6. The lead wires 20 are connected to a proper power supply source, and the light emission diodes 6 are coated with a proper protective film. The cylindrically-shaped ring 18 is increased in length so as to form a pipe-shaped one as shown in FIG. 7C, whereby the light emission diodes 6 may be mounted around the outer peripheral surface of such pipe. The ring or pipe 18 attached to the nozzle 17 as above forms a nozzle top portion newly. The number of the light emission diodes 6 may be small if the light emission diode produces a large output, while it is large if the light emission diode produces a small output. The light emission diode 6 can produce a large output by employing an oscillation pulse of large amplitude for intermittently driving the light emission diodes. If the light emission diode is driven by the oscillation pulse, the heat radiation is enhanced to more effectively prevent bacteria from proliferating. If the base plate 19 is formed of a ceramic base plate which is good in heat radiation, the light emission diodes may be driven continuously.

In the embodiment of this type, the light receiving element is provided at the position opposed to the light emission diodes 6 and the outputs therefrom is supplied to an indicator (lamp, etc.) located at the position easy to see the same, thus making it possible to confirm whether the light emission diodes are actually driven to emit rays of light.

Figure 8:
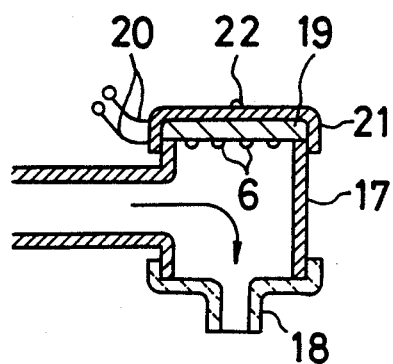
FIG. 8 is a cross-sectional view illustrating the seventh embodiment of the present invention.

FIG. 8 is a cross-sectional view illustrating the seventh embodiment of the present invention. In the figure, like parts corresponding to those of FIG. 7 are marked with the same references. There are shown a cap 21 which is integrally formed together with the base plate 19 and the light emission diodes 6 and a colored light emission diode 22 for confirming the above-mentioned light emission. In this embodiment, the cap 21 is not necessarily made of material having light transmission property, and the nozzle mouth 18 of light transmission property is attached to the top portion of the nozzle 17. This nozzle mouth 18 may be formed as a shower head having a number of small openings.

Figure 9:
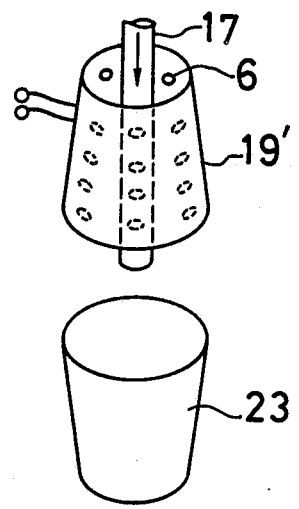
FIG. 9 is a perspective view illustrating the eighth embodiment of the present invention.

FIG. 9 is a perspective view illustrating the eighth embodiment of the present invention. Also in this figure, like parts corresponding to those of the sixth embodiment will be identified by the same reference numerals. This embodiment is the application to the nozzle 17 of light transmission property which is long in length. A reversed glass-shaped base plate 19' on the inner side of which the light emission diodes 6 are arranged is mounted to the top portion of the nozzle 17 by proper means. According to this embodiment, not only the exit of the nozzle 17 but also the peripheral portion and the inside of the opening of a glass 23 located above and below the same can be irradiated.

The above-mentioned sixth to eighth embodiments are described as representative examples and various modifications and variations can therefore be effected without departing from the scope of the present invention. For example, the top portion of the nozzle having light transmission property may be formed as a spirally-shaped or zigzag-shaped one and the whole of such portion may be irradiated in the manner same as that shown in FIG. 9. Further, in the embodiment shown in FIG. 7, the mouth of the nozzle top portion 18 is closed and the light emission diodes are mounted on the closed surface so that upon non-use of the nozzle, the light emission diodes are inserted into the top of the nozzle 17.

Figure 10:
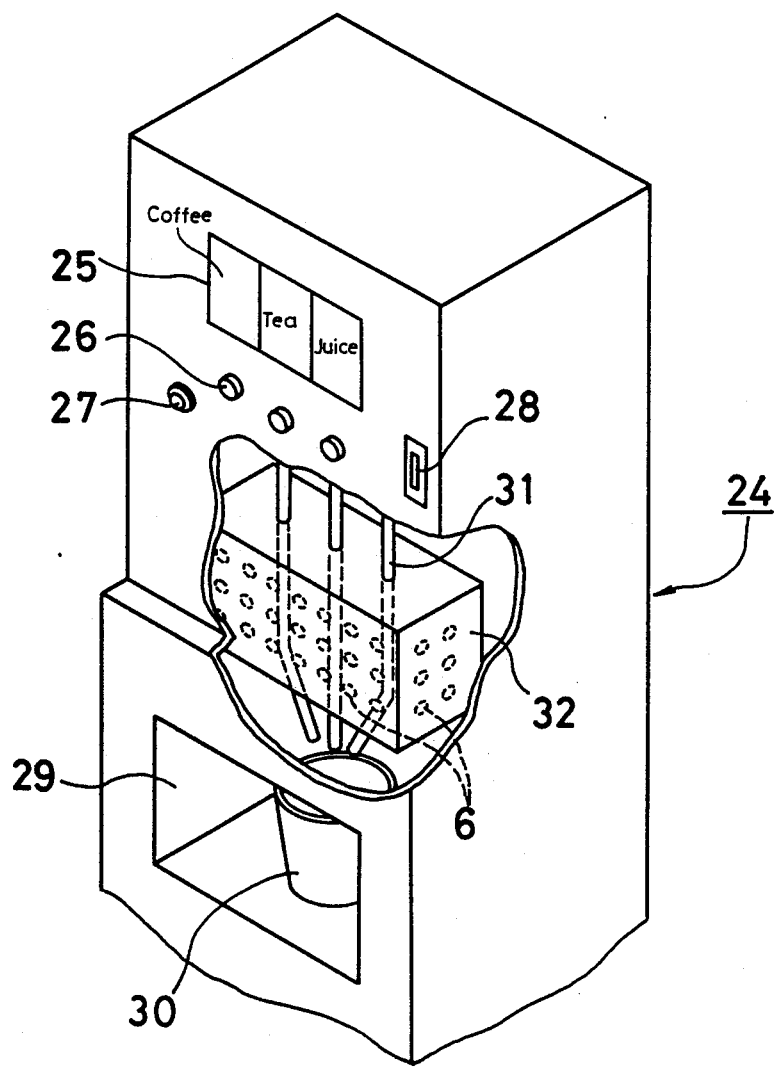
FIG. 10 is a partly cut-away perspective view illustrating the ninth embodiment of the present invention.

FIG. 10 is a partially cut-away perspective view illustrating the ninth embodiment of the present invention which is applied to an automatic drink vending machine. Referring to the figure, 24 generally shows an automatic drink vending machine, 25 a display panel indicative of the kinds of soft drinks to sell, 26 selection buttons, 27 a confirmation lamp, 28 a slit into which coins are thrown, 29 a large opening from which a desired drink is drawn out, 30 a glass, 31 drink supplying pipes of light transmission property for supplying drinks therethrough and 32 a box-shaped base plate on the inner surface of which the light emission diodes 6 are mounted. In this kind of automatic vending machine, the user picks up a glass from a glass holder, not shown, one by one and puts it in the opening 29. When the user throws coins into the slit 28 and presses the button 26 located under the display of the desired drink, the selected drink of constant quantity contained in each tank, not shown, is supplied through the individual drink supplying pipe 31 and dropped into the glass 30.

The box-shaped base plate 32 is disposed so as to surround the three drink supplying pipes 31 of light transmission property, and the top portion or the bottom portion or both top and bottom portions thereof are made open. Alternatively, the whole thereof may be closed tightly. While the drink supplying pipe 31 of light transmission property is made of, for example, resinous material so as to enable the whole thereof to pass therethrough rays of light, only the portion that should be kept in a sanitary condition is made of material having light transmission property. With this structure, the light emission diodes 6 can irradiate the inside of the drink supplying pipe. Further, they can irradiate the portion near the mouth of the pipe if the bottom of the box-shaped base plate 32 is opened, thus suppressing bacteria from proliferating at the portion irradiated by rays of light.

In this embodiment, the light receiving elements are disposed within the box-shaped base plate 32 to receive rays of light emitted from the light emission diodes 6, and also connected to the confirmation lamp 27 installed on the front panel of the automatic vending machine 24, thus making it possible to confirm from the outside whether or not the light emission diodes 6 are actually being operated to emit rays of light. This arrangement, however, may be omitted. While in the illustrated embodiment the base plate 32 to which the light emission diodes 6 are mounted is formed as a boxed-shaped one, it may be cylindrically-shaped base plate. Further, such a version is also possible that when the user holds the glass 30, the light emission diodes are disabled so as to protect the user's hands from the irradiation of light.

The present invention is not limited to the above-mentioned ninth embodiment but can be applied to pipes for supplying therethrough various kinds of drinks (including the drinking water) that must be protected from the contamination.

According to the present invention, as set forth above, since bacteria can be prevented from proliferating within the small tank by the simplified arrangement, the present invention is not limited to the above-mentioned embodiments but can be widely applied to various tanks such as the tank of small capacity used in the automatic drink vending machine, the container for purified water, the supplying tank for flush toilet and the water tank for flush toilet of washing douche and drier type, and these small tanks can be efficiently maintained in a clear and sanitary condition. In addition, as compared with the ultraviolet lamp, the sanitary device of the present invention requires less space and has a lifetime of more than ten times that of the ultraviolet lamp.

Since the article to be kept in the container can be maintained in a clear, sanitary condition by the simplified arrangement and the light sources can be attached to the container itself unlike the case where the ultraviolet lamp is employed, the sanitary device of the present invention is suitable for the small container and can sterilize the small container efficiently as compared with the ultraviolet lamp.

Also, since various kinds of nozzle mouths that should be maintained in a sanitary condition are prevented from being contaminated by the proliferation of bacteria and the light emission diodes are arranged so as not to irradiate the unnecessary portion, the sanitary device of the present invention is enhanced in efficiency and is economical.

Further, the pipes for supplying therethrough the drinking water and various kinds of drinks can be maintained in a sanitary condition. Furthermore, since the light emission diodes ar utilized as the light source, the sanitary device can be simplified in construction. Each of the light emission diodes is small in size so that a number of light emission diodes do not need large space. Since the output from each of the light emission diodes can be increased by the pulse oscillation of large amplitude, the number of the light emission diodes can be decreased more. In addition, the sanitary device of the invention can be prevented from being broken and also protected from the harmful insects.

While the light emission diode is employed as the element for emitting rays of light which can prevent the proliferation of bacteria in each of the above-mentioned embodiments, the light emitting element of the present invention is not limited to the light emission diode but may be other elements such as electro-luminescence element which can achieve the same actions.

Rays of light for preventing the proliferation of bacteria may be visible rays of light and infrared rays emitted from semiconductor lasers.

Alternatively, bacteria can be prevented from proliferating more efficiently by the application of the magnetic field to the optical path.

Furthermore, such a version is possible that metal or non-metal for producing electron by the irradiation of rays of light is provided on the surface which is irradiated by rays of light, whereby photoelectron is produced to prevent the proliferation of bacteria more efficiently. Also, ion action is caused by the electron and this ion action is utilized to purify or deodorize air, water or the like.

I claim:

1. A sanitation device comprising means for supporting objects to be sanitized and a plurality of semiconductor light emission diodes, each emitting rays of light which prevent proliferation of bacteria, said semiconductor light emission diodes being arranged in such proximity to said objects as to irradiate said objects with a light intensity sufficient to prevent growth of bacteria in or on said objects.

2. The sanitation device according to claim 1 wherein said means for supporting said objects comprises a container and said semiconductor light emission diodes are mounted within said container.

3. The sanitation device according to claim 1 wherein said means for supporting said objects is a container, being at least in part transparent to the passage of light from said semiconductor light emission diodes and said light emitting diodes are mounted on the exterior of said container adjacent said transparent part thereof.

4. The sanitation device according to claim 1 wherein said semiconductor light emission diodes emit a visible light.

5. The sanitation device according to claim 1 wherein said semiconductor light emission diodes emit infrared light.

6. The sanitation device according to claim 1 wherein said semiconductor light diodes emit ultraviolet light.

7. The sanitation device comprising means for supporting objects to be sanitized and a plurality of electro-luminescence elements each emitting rays of light which prevent proliferation of bacteria, said electro-luminescence elements being arranged in such proximity to said objects as to irradiate said objects with a light intensity sufficient to prevent growth of bacteria in or on said objects.

8. The sanitation device according to claim 7 wherein said means for supporting said objects comprises a container and said electro-luminescence element are mounted with inset container.

9. The sanitation device according to claim 7 wherein said means for supporting said objects is a container, being at least in part transparent to the passage of light from said electro-luminescence elements and said electro-luminescence elements are mounted on the exterior of said container adjacent said transparent part thereof.

10. The sanitation device according to claim 7 wherein said electro-luminescence elements emit visible light.

11. The sanitation device according to claim 7 wherein said electro-luminescence elements emit infrared light.

12. The sanitation device according to claim 7, wherein said electro-luminescence elements emit ultraviolet light.

13. The sanitation device comprising means for supporting objects to be sanitized and a plurality of semiconductor lasers, each emitting rays of light which prevent proliferation of bacteria, said semiconductor lasers being arranged in such proximity to said objects as to irradiate said objects with a light intensity sufficient to prevent growth of bacteria in or on said objects.

14. The sanitation device according to claim 13, wherein said means for supporting said objects comprises a container and said semiconductor lasers are mounted with inset container.

15. The sanitation device according to claim 13, wherein said means for supporting said objects is a container, being at least in part transparent to the passage of light from said semiconductor lasers and said semiconductor lasers are mounted on the exterior of said container adjacent said transparent part thereof.

16. The sanitation device according to claim 13, wherein said semiconductor lasers emit visible light.

17. The sanitation device according to claim 13, wherein said semiconductor lasers emit infrared light.

18. The sanitation device according to claim 13, wherein said semiconductor lasers emit ultraviolet light.

* * * * *